United States Patent [19]

Laruelle et al.

[11] Patent Number: 4,568,754
[45] Date of Patent: Feb. 4, 1986

[54] PROCESSES FOR THE PREPARATION OF DERIVATIVES OF 2-[3-(3-INDOLYL) 2-AMINO PROPIONYLOXY] ACETIC ACID

[76] Inventors: Claude Laruelle, Avenue Bellevue 06270, Villeneuve Loubet; Marcel Lepant, L'Escoundu, Allée Clairefontaine 06140, Vence, both of France

[21] Appl. No.: 587,043

[22] Filed: Mar. 7, 1984

Related U.S. Application Data

[62] Division of Ser. No. 342,929, Jan. 26, 1982, Pat. No. 4,456,611.

[30] Foreign Application Priority Data

Feb. 2, 1981 [FR] France ............................. 81 01931

[51] Int. Cl.$^4$ ........................................... C07D 209/20
[52] U.S. Cl. .................................................. 548/497
[58] Field of Search ......................................... 548/497

[56] References Cited

U.S. PATENT DOCUMENTS 3,988,341 10/1976 Saari et al. ......................... 546/221

Primary Examiner—Glennon H. Hollrah
Assistant Examiner—D. B. Springer
Attorney, Agent, or Firm—Browdy and Neimark

[57] ABSTRACT

Derivatives of 2-[3-(3-indolyl 2-amino propionyloxy] acetic acid corresponding to the following general formula I:

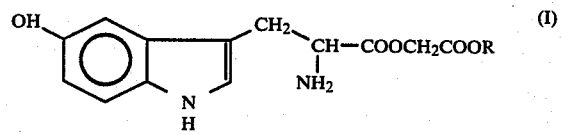

in which R represents a hydrogen atom, a linear or branched alkyl radical including 1 to 12 carbon atoms, or a mono-alicyclic or polycyclic radical containing 5 to 16 carbon atoms, possibly linked by a methylene radical, and their pharmaceutically acceptable addition salts, are useful as medicaments for palliating deficiency of the serotoninergic system.

7 Claims, No Drawings

PROCESSES FOR THE PREPARATION OF DERIVATIVES OF 2-[3-(3-INDOLYL) 2-AMINO PROPIONYLOXY] ACETIC ACID

This is a division of application Ser. No. 342,929 filed Jan. 26, 1982, U.S. Pat. No. 4,456,611, issued 6/26/84.

The present invention relates to novel derivatives of 2-[3-(3-indolyl)2-amino propionyloxy]acetic acid, and to processes for their preparation, and medicaments containing them and the method of treating animals therewith.

The role which serotonin (or 5-hydroxy tryptamine) plays in the biological activity of living creatures is known. Besides regularizing intestinal motility, having an action on smooth muscle, and vasoconstrictor effects, it also exerts psychomotor and psychomimetic effects, thus constituting a veritable neurohormone which occupies an important place as a chemical mediator in brain activity.

Deficiency of the serotoninergic system (serotonin is principally secreted by the argentaffin cells, in particular at the level of the digestive tract and especially at the level of the encephalon) can cause very serious psychiatric and neurological disorders. Since it is impossible to supply preformed serotonin to insufficient serotoninergic systems, its immediate precursor, namely 5-hydroxy-tryptophane (5 HTP) whose formula is shown below, was until now still the best vector similar to serotonin.

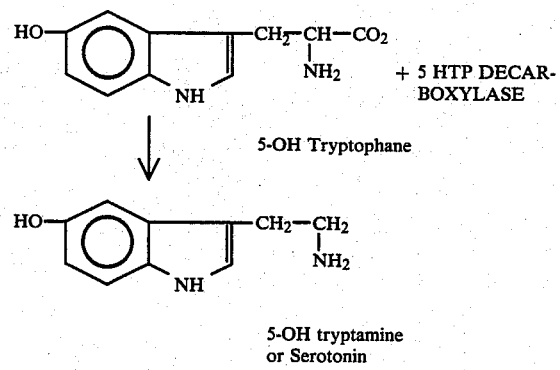

5-OH Tryptophane

5-OH tryptamine or Serotonin

Such administration constitutes however a considerable drawback: the decarboxylase transforming the 5-hydroxytryptophane into serotonin, being widely distributed in the peripheral system, results in a considerable loss of 5-HTP capable of passing into the brain.

It is an object of the present invention therefore to provide novel derivatives of 5-HTP more resistant to peripheral decarboxylation and regenerating 5-HTP at the cerebral level, thus increasing the balance of passage through the blood-brain barrier.

It is hence a further object of the present invention to permit—without requiring the introduction of peripheral decarboxylase inhibitor—an increase in the endogenous serotonin level in the brain by considerably reducing peripheral loss of 5-HTP.

According to the present invention there are provided derivatives of 2-[3-(3-indolyl)2-amino propionyloxy]acetic acid corresponding to the following general formula I:

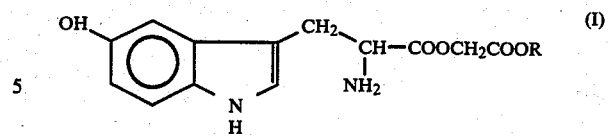

in which R represents:
a hydrogen atom,
a linear or branched alkyl radical containing 1 to 12 carbon atoms,
or a mono-alicyclic polycyclic radical containing 5 to 16 carbon atoms or an adamantyl, bornyl, camphyl or menthyl radical possibly connected by a methylene radical,
and their pharmaceutically acceptable additional salts.

The compounds according to the present invention are remarkable medicaments useful in human and veterinary therapeutics and particularly in the psychiatric field.

According to another aspect of the present invention there is provided a process for the preparation of derivatives according to the present invention, in which process the phenol function and/or the amine function is blocked by $R_2OCO-$ radical where $R_2$ represents an aliphatic or aromatic group designed to protect the phenol and/or amine function, wherein the starting acid is esterified by a compound corresponding to the formula:

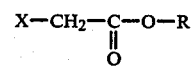

in which:
X represents a halogen atom and preferably a chlorine or bromine atom, and
R has the same meaning as above, and wherein the amine function and/or the phenol function are then unblocked.

According to the preferred embodiment of the process according to the present invention, the amine and-/or phenol functions are blocked by means of reagents having the formula:

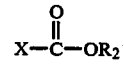

$R_2$ and X having the same meaning as previously.

The reaction diagram can be represented in the following manner:

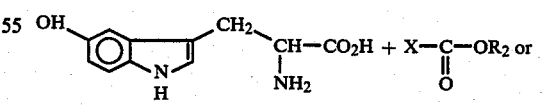

-continued

(VI)

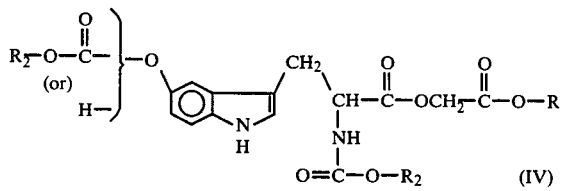

Then by deblocking the OH at 5 and/or the $NH_2 \longrightarrow$

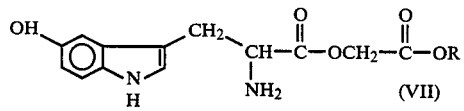

In another advantageous embodiment according to the invention, the condensation of the 3-(5-hydroxy 3-indolyl) acid derivatives with the alkylating agent is carried out in the presence of a base accepting a hydro halogenic acid and in an aprotic solvent such as dimethylformamide or the like.

In accordance with the invention, the deblocking of the $NH_2$ and/or OH functions is carried out by acid treatment.

In another modification of the process according to the present invention, the deblocking of the $NH_2$ and/or OH functions is effected by catalytic hydrogenation.

The chemical reactions effected do not modify the stereochemistry at the level of the asymetric carbon bearing the primary amine nitrogen. Neither is racemisation of the optically active derivatives thereof.

Other than the foregoing features, the invention comprises yet other features, which will emerge from the description which follows.

The present invention will be better understood with the aid of the additional description which follows, in which will be found examples of practising the process of preparation of novel derivatives according to the invention, as well as a description of pharmacological experiments.

It must be well understood however that these examples are given purely by way of illustration of the products and processes according to the invention, but do not constitute in any way a limitation thereof.

It is to be noted that the NMR$^1$H spectra of the product of formula I all have the following common characteristic signals: 6.6 to 7.6 ppm (m) (aromatics)(4H); 4.7 ppm (s)—O—$CH_2$—C=O; 3.8 ppm (m)×$NH_2$—CH—COO (1H); 3.1 ppm (m) $CH_2$—CH ($NH_2$)—COO.

The IR (K Br) spectra have the following common characteristic bands: 3300 cm$^{-1}$ (OH, $NH_2$), 1745–1755 cm$^{-1}$ (esters).

EXAMPLE 1

Ethyl D,L-2-[3-(5-hydroxy 3indolyl)2-amino propionyloxy]acetate [(I); R=$C_2H_5$]

(a) D,L-3-(5-benzyloxycarbonyloxy 3-indolyl)2-benzyloxycarbonylamino propionic acid Under an atmosphere of nitrogen 220 g of DL 5-hydroxy tryptophane (1 mole) are dissolved in 5 liters of water and 40 g of sodium hydroxide (1 mole). 660 ml of benzyl chloroformate in 50% solution in toluene are run in four hours into this stirred solution whilst keeping the pH around 9.5 by the addition of 2N sodium hydroxide. After some hours of stirring at room temperature, the aqueous phase is decanted, washed with ether, then run into an excess of iced dilute hydrochloric acid, the precipitate is filter, washed and dried. The crude product is purified in a propanol-water mixture then recrystallized in 20 volumes of ethanol.

A first crop of 133 g of white crystals of mp 135°/140° C. (Kofler) is obtained (yield=31%) and a second crop of 200 g of melting point 110°/120° C. (total yield=72%) useful for the syntheses following was obtained.

(b) Ethyl D,L-3-[3-(5-benzyloxycarbonyloxy 3-indolyl)2-benzyloxycarbonylamino propionyloxy]acetate A mixture is made of:
100 g (0.2 mole) of D,L-3-(5-benzyloxycarbonyloxy 3-indolyl)2-benzyloxycarbonylamino propionic acid(prepared according to Example 1-a),
600 ml of dimethylformamide
40 ml (0.2 mole of dicyclohexylamine,
21.1 ml of (0.2 mole) of ethyl chloracetate,
1 g of sodium iodide.

After 20 hours of stirring at ordinary temperature, the precipitate of dicyclohexylamine hydrochloride was filtered, washed with ethyl acetate and the solvents evaporated off under reduced pressure. The oily residue was taken up again in 1 liter of toluene and washed successively with water, with dilute hydrochloric acid, then with dilute sodium bicarbonate. After drying, the solvent was evaporated and the residual oil was crystalized in hexane and then recrystallized in xylene. A white crystalline product of mp=74° C. (Kofler) was obtained.

(c) Ethyl D,L-2-[3-(5-hydroxy 3-indolyl)2-amino propionyloxy]acetate 25 g (0.043 mole) of the preceding derivative was hydrogenated in 500 ml of isopropyl alcohol in the presence of 2.5 g of 5% palladium on charcoal. When the theoretical amount of hydrogen was absorbed, the catalyst was filtered off, it was evaporated, taken up in ethyl acetate and washed with water. After evaporation of the solvent, the oily residue was recrystallized in cyclohexane. 60% of pure product melting at 93°/94° C. was obtained.

(d) D,L-3-(5-hydroxy 3-indolyl)2-benzyloxycarbonylamino propionic acid [(III), OH-5 and R'=benzyl]

At ordinary temperature under a nitrogen atmosphere 44 g (0.2 mole) of DL-5-hydroxy tryptophane was dissolved in one liter of distilled water and 6 g of pure sodium hydroxide, then run in 2 hours into 28.5 ml of benzyl chloroformate in solution in 150 ml of acetone keeping the pH of the solution at 9.5 by the addition of dilute sodium hydroxide. After some hours of stirring at ordinary temperature, the acetone was evaporated off under reduced pressure and the alkaline aqueous solution was run into an excess of iced dilute hydrochloric acid. The precipitate was filtered off, washed rapidly and dried protected from air and light. The crude product (R$^{dt}$ 100%) was purified by chromatography on silica protected from light by elution with a benzene methanol mixture and 26 g ($R^{dt}=37\%$) of pure product of mp=80° C. was obtained.

(e) Ethyl D,L-2-[3-(5-hydroxy 3-indolyl)2-benzyloxycarbonylamino propionyloxy]acetate For 20 hours at ordinary temperature the following mixture was stirred:
17.7 g (0.05 mole) of DL 3-(5-hydroxy 3-indolyl)2-benzyloxycarbonylamino propionic acid prepared according to Example 1-d,
0.5 g of sodium iodide
6.1 g (0.05 mole) of ethyl chloracetate
10 ml of dicyclohexylamine,
100 ml of dimethylformamide.

It was then treated according to Example 1-b. The residual crude oil was chromatographed on silica by eluting with a benzene/ethyl acetate mixture. 16.2 g of thick oil showing only a single spot of Rf 0.55 by TLC on silica gel in the solvent system: toluene 80, ethyl formate 40, formic acid 5, was obtained.

The NMR$^1$H spectrum recorded in solution in DMSO d$^6$ shows the following characteristic signals: 7.3 ppm (s) (5H) ar. of benzyl-6.8/7.2 ppm (m) (4H), ar. of indole-5.2 ppm (s) (2H) CH$_2$ of benzyl-4.7 ppm (s) (2H)—O—CH$_2$—C=O-4.2 ppm (m) (2H) of CH$_2$—C$_3$-4.2 ppm (m) (1H) of CH in α of

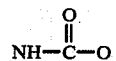

-3.3 ppm (m) (2H) CH$_2$—CH-1.2 ppm CH$_3$(t) (3H).

(f) Ethyl D,L-2-[3-(5-hydroxy 3-indolyl)2-amino propionyloxy]acetate 8.8 g (0.020 mole) of the product previously obtained was hydrogenated in solution in 150 ml of isopropyl alcohol in the presence of 1 g of 5% palladium on charcoal. It was then treated according to Example 1-c and the compound of the titer of mp 93°/94° C. was obtained identical with that prepared according to the sequence 1-a, 1-b, 1-c.

EXAMPLE 2

Butyl D,L-2-[3-(5-hydroxy 3-indolyl)amino propionyloxy]acetate [(I), R=C$_4$H$_9$]

(a) Butyl D,L-2-[3-(5-benzyloxycarbonyloxy 3-indolyl)2-benzyloxycarbonylamino propionyloxy]acetate At ordinary temperature the following were mixed:
100 g (0.2 mole) of D,L3-(5-benzyloxycarbonyloxy 3-indolyl)2-benzyloxycarbonylamino propionic acid (prepared according to Example 1-a),
40 ml (0.2 mole) of dicyclohexylamine
28.3 ml (0.2 mole) of butyl chloracetate
600 ml of dimethylformamide
2 g sodium iodide,
and it was then treated according to the technique described in Example 1-b.

125 g of crude product was obtained which can be purified by crystallization in isopropanol and then in ethanol. A product of mp 90° C. (Kofler) was thus obtained.

(b) Butyl D,L-2-[3-(5-hydroxy 3-indolyl)2-amino propionyloxy]acetate 25 g of the previously obtained product was hydrogenated in 500 ml of isopropyl alcohol in the presence of 2.5 g of 5% alladium on charcoal. When the theoretical amount of hydrogen had been absorbed, the catalyst was filtered off, it was evaporated and then taken up again with ethyl acetate. After washing with water, the solvent was evaporated off. The product was purified by chromatography on silica, and 50% of product melting at 90° C. was obtained.

EXAMPLE 3

Octyl D,L-2-[3-(5-hydroxy 3-indolyl)2-amino propionyloxy]acetate [(I), R=C$_8$H$_{17}$]

(a) Octyl D,L-2-[3-(5-benzyloxycarbonyloxy 3-indolyl)2-benzyloxycarbonylamino propionyloxy]acetate For 20 hours the following mixture was stirred:
100 g (0.2 mole) of D,L-3-(5-benzyloxycarbonyloxy 3-indolyl)2-benzyloxycarbonylamino propionic acid,
600 ml of dimethylformamide
40 ml (0.2 mole) of dicyclohexylamine,
2 g of sodium iodide
41.3 g (0.2 mole) of octyl chloracetate,
and it was then treated according to the technique described in Example 1-b. The crude product, recrystallized in xylene gave 36 g of beautiful white crystals of mp 96° C.

(b) Octyl D,L-2-[3-(5-hydroxy 3-indolyl)2-amino propionyloxy]acetate

At atmospheric pressure 50 g (0.075 mole) of the previously obtained compound was hydrogenated in 500 ml of isopropyl alcohol in the presence of 5 g of 5% palladium on charcoal. When the theoretical amount of hydrogen had been consumed, the catalyst was filtered off, was evaporated to dryness and taken up again in ethyl acetate. The organic layer was washed with water, treated in the dark and then evaporated. A crude oil was obtained which was crystallized in cyclohexane. mp=91° C.

EXAMPLE 4

Dodecyl D,L-2-[3-(5-hydroxy 3-indolyl)2amino propionyloxy]acetate [(I), R=C$_{12}$H$_{25}$]

(a) Dodecyl D,L-2-[3-(5-benzyloxycarbonyloxy 3-indolyl)2-benzyloxycarbonylamino propionyloxy]acetate There were mixed together:
25 g (0.05 mole) of D,L-3-(5-benzyloxycarbonyloxy 3-indolyl)2-benzyloxycarbonylamino propionic acid (prepared according to Example 1-a),
200 ml of dimethylformamide
10 ml of dicyclohexylamine,
500 mg of sodium iodide,
13.2 g of dodecyl chloracetate,
it was then treated according to the technique described in Example 1-b. The product can be recrystallized in an isopropanol hexane mixture.

(b) Dodecyl D,L-2-[3-(5-hydroxy 3-indolyl)2-amino propionyloxy]acetate 25 g of the product previously obtained was hydrogenated in 500 ml of isopropyl alcohol in the presence of 2.5 g of 5% palladium on charcoal. When the theoretical amount of hydrogen had been absorbed, the catalyst was filtered off, it was then evaporated to dryness, taken up again by ethyl acetate and washed with water. By treatment with the hydrochloric acid, it was possible to isolate the hydrochloride directly mp=122°/4° C.

EXAMPLE 5

Methyl L-2-[3-(5-hydroxy 3-indolyl)2-amino propionyloxy]acetate [(I), R=CH$_3$]

(a) L-(5-benzyloxycarbonyloxy 3-indolyl)2-benzyloxycarbonylamino propionic acid

Under a nitrogen atmosphere 220 g of (L)5-hydroxy tryptophane was dissolved in 5 liters of water and treated with benzyl chloroformate by the process used in Example 1-a for the racemic compound. In this way 93% of crude oil was obtained. The crude product was purified by the technique employed for the D-L compound. 40% of white crystals were obtained melting at 145°/6° C.

$[\alpha]_D^{21} = -7.1°$(C=0.5% absolute ethanol)
$[\alpha]_D^{21} = -9.9°$(C=1% acetone).

(b) Methyl L-2-[3-(5-benzyloxycarbonyloxy 3-indolyl)2-benzyloxycarbonylamino propionyloxy]acetate For 20 hours the following mixture was stirred:
50 g (0.1 mole) of L-3-(5-benzyloxycarbonyloxy 3-indolyl)2benzyloxycarbonylamino propionic acid (prepared according to Example 5-a)
300 ml of dimethyl formamid,
20 ml of dicyclohexylamine,
1 g of sodium iodide,
11 g (0.1 mole) of methyl chloracetate,
and it was treated according to Example 1-b.

After evaporation of the solvent, it was purified by chromatography on silica by eluting with a benzene ether mixture. A pure oil having only a single spot of Rf 0.6 in C.C.M. on a silica plate in the system toluene 80, ethyl formate 40, formic acid 5 was obtained and which was used directly in the following step.

(c) Methyl L-2-[3-(5-hydroxy 3-indolyl)2-amino propionyloxy]acetate 28 g (0.05 Mole) of the preceding product was hydrogenated in solution in isopropanol and in the presence of 2.5 g of 5% palladium on charcoal. When the theoretical amount of hydrogen had been fixed, the catalyst was filtered off, the solvent was evaporated, and it was taken up in ethyl acetate which was washed with water, then after evaporation of the solvent, recrystallized in benzene. 50% of white crystals melting at 125° C. (Kofler) $[\alpha]_D^{25} = -59°$(acetone 1%) were obtained.

EXAMPLE 6 ethyl L-2-[3-(5-hydroxy 3-indolyl)2-amino propionyloxy]acetate [(I), R=C$_2$H$_5$]

(a) Ethyl L-2-[3-(5-benzyloxycarbonyloxy 3-indolyl)2-benzyloxycarbonylamino propionyloxy]acetate The following mixture was stirred for 20 hours:
50 g (0.1 mole) L-3-(5-benzyloxycarbonyloxy 3-indolyl)2-benzyloxycarbonylamino propionic acid obtained according to Example 5-a,
300 ml of dimethylformamid,
20 ml of dicyclohexylamine,
1 g of sodium iodide,
10.5 ml of ethyl chloracetate,
and it was treated according to Example 1-b after complete evaporation of the solvent. 51 g of a brown oil was obtained showing only one spot of Rf=0.6 in thin layer chromatography on a Kieselgel plate in the system toluene 80, ethyl formate 40, formic acid 5. The infrared spectrum of the product included two characteristic heavy bands at 3400 cm$^{-1}$ and 1740 cm$^{-1}$ and a $[\alpha]_D^{25} = -22.55°$(1% in ethanol).

(b) Ethyl L-2-[3-(5-hydroxy 3-indolyl)2-amino propionyloxy]acetate

Under atmospheric pressure 49 g (0.0854 mole) of the previously obtained product was hydrogenated in solution in isopropanol and in the presence of 2.5 g of 5% palladium on charcoal. When the theoretical amount of hydrogen had been fixed, the catalyst was filtered off, the solvent was evaporated and it was taken up with ethyl acetate was washed with water, treated in the dark and then evaporated. The residue taken up again in isopropyl alcohol was converted into the hydrochloride which crystallized in the cold, filtered, washed and dried. 20.8 g (yield 71%) of the hydrochloride of melting point 257°/260° was obtained. This hydrochloride treated with dilute ammonia, liberated the base, which was filtered, washed with water and dried. Beautiful white crystals of mP=136° were obtained showing only a single spot of Rf=0.4 in TLC on Kieselgel in the system acetonitrile 130, water 15, acetic acid 5-$[\alpha]_D^{25} = -60.4°$(1% acetone).

EXAMPLE 7 n-propyl L-2-[3-(5-hydroxy 3-indolyl)2-amino propionyloxy]acetate [(I), R=C$_3$H$_7$]

(a) Propyl L-2-[3-(5-hydroxy 3-indolyl)2-amino propionyloxy]acetate

For 20 hours the following mixture was stirred:
50 g (0.1 mole) L-3-(5-benzyloxycarbonyloxy 3-indolyl)2benzyloxycarbonylamino propionic acid obtained according to Example 5-a,
300 ml of dimethylformamide,
20 ml of dicyclohexylamine,
1 g of sodium iodide,
12 ml of n-propyl chloracetate,
and treated according to Example 1-b. After evaporation of the solvent, the crude oil was purified by chromatography on silica by eluting with a benzene/ether mixture. 60% of pure oil having only a single spot of Rf 0.5 by TLC on silica gel in the system: toluene 80, ethyl formate 40, formic acid 5, $[\alpha]_D^{25} = -25$(1% Ethanol), was obtained.

(b) n-propyl L-2-[3-(5-hydroxy 3-indolyl)2-amino propionyloxy]acetate

Under atmospheric pressure 29.5 g (0.05 mole) of the previously obtained product was hydrogenated in 500 ml of isopropyl alcohol in the presence of 2.5 g of 5% palladium on charcoal. When the theoretical amount of hydrogen had been fixed, the catalyst was filtered off, was evaporated, taken up again with ethyl acetate then washed with water. After evaporation of the solvent and recrystallization in benzene, 55% of pure product melting at 97° C. and $[\alpha]_D = -58.5°$(acetone 1%) was obtained.

EXAMPLE 8 n-butyl L-2-[3-(5-hydroxy 3-indolyl)2-amino propionyloxy]acetate [(I), R=C$_4$H$_9$]

(a) butyl L-2-[3-(5-benzyloxycarbonyloxy 3-indolyl)2-benzyloxycarbonylamino propionyloxy]acetate The following mixture was stirred for 20 hours:
50 g (0.1 mole) L-(5-benzyloxycarbonyloxy 3-indolyl)2-benzyloxycarbonylamino propionic acid prepared according to Example 5-a,
20 ml of dicyclohexylamine,
14.2 ml (0.1 mole) of butyl chloracetate,
300 ml of dimethylformamide,
1 g of sodium iodide,
and was then treated by the technique described in Example 1-b. An oil was obtained (yield=80%) having only a single spot in TLC on silica gel of Rf=0.5 in the system: toluene 80, ethyl formate 40, formic acid 5.

(b) n-butyl L-2-[3-(5-hydroxy 3-indolyl2-amino propionyloxy]acetate

Under atmospheric pressure 37.5 g (0.057 mole) of the previously obtained product was hydrogenated in 500 ml of isopropyl alcohol in the presence of 2.5 g of 5% palladium on charcoal. When the theoretical amount of hydrogen had been absorbed, the catalyst was filtered off, it was evaporated, taken up again with ethyl acetate and washed with water. After evaporation of the solvent, 23.5 g of crude oil were obtained, which was taken up with ethyl acetate, washed with water and then evaporated. 51% of pure product melting at 96° C. (Kofler) $[\alpha]_D^{25}$=+2.7°(Ethanol 1%);=−51°(acetone %) were obtained.

EXAMPLE 9 n-pentyl L-2-[3-(5-hydroxy 3-indolyl)2-amino propionyloxy]acetate [(I), R=C$_5$H$_{14}$]

(a) pentyl L-2-[3-(5-benzyloxycarbonyloxy 3-indolyl)2-benzyloxycarbonylamino propionyloxy]acetate The following mixture was stirred for 20 hours:
50 g (0.1 mole) of L-3-(5-benzyloxycarbonyloxy 3-indolyl)2-benzyloxycarbonylamino propionic acid, prepared according to Example 5-a.
20 ml of dicyclohexylamine (0.1 mole),
1 g of sodium iodide,
16.5 g (0.1 mole) of pentyl chloracetate,
300 ml of dimethylformamide,
and it was then treated according to Example 1-b. The crude oil was purified by chromatography on silica by eluting with a benzene ether mixture. 62% of pure oil was obtained having only a single spot of Rf 0.55 in C.C.M. on silica gel in the previously described solvent system.

(b) n-pentyl L-2-[3-(5-hydroxy 3-indolyl)2-amino propionyloxy]acetate 30 g (0.05 mole) of product obtained in (a) was hydrogenated in 400 ml of isopropyl alcohol in the presence of 2.5 g of 5% palladium on charcoal. When the theoretical amount of hydrogen had been absorbed, the catalyst was filtered off, it was evaporated to dryness and taken up with ethyl acetate which was washed with water. After evaporation of the solvent, the crude oil was crystallized in benzene. 45% of pure product was obtained melting at 97° C. $[\alpha]_D^{22}$=−50.5°(acetone 1%).

EXAMPLE 10 n-hexyl L-2-[3-(5-hydroxy 3-indolyl)2-amino propionyloxy]acetate [(I), R=C$_6$H$_{13}$]

(a) n-hexyl L-2-[3-(5-benzyloxycarbonyloxy 3-indolyl)2-benzyloxycarbonylamino propionyloxy]acetate For 20 hours at ordinary temperature the following mixture was stirred:
50 g (0.1 mole) of L-3-(5-Benzyloxycarbonyloxy 3-indolyl)2-benzyloxycarbonylamino propionic acid prepared according to Example 5-a,
20 ml of dicyclohexylamine (0.1 mole),
1 g of sodium iodide,
18 g (0.1 mole) of n-hexyl chloracetate,
300 ml of dimethylformamide,
it was then treated according to Example 1-b. The crude oil was chromatographed on silica by a benzene ether mixture. The pure fraction represented a 66% yield, it only showed a single spot in TLC on silica gel in the usual solvent system, and is used directly for the following step.

(b) n-hexyl L-2-[(hydroxy 3-indolyl)2-amino propionyloxy]acetate

Under atmospheric pressure 20 g (0.047 mole) of the previously obtained product was hydrogenated in solution in 500 ml of isopropyl alcohol in the presence of 2.5 g of 5% palladium on charcoal. When the theoretical amount of hydrogen had been absorbed, the catalyst was filtered off, the alcohol was evaporated, it was taken up with ethyl acetate which was washed carefully with water. After evaporation of the solvent, it was crystallized in benzene and 70% of wwhite crystals melting at 99° C. (Kofler) and $[\alpha]_D^{22}$=−51°(acetone 1%), were obtained.

EXAMPLE 11 n-heptyl L-2-[3-(5-hydroxy 3-indolyl)2-amino propionyloxy]acetate [(I), R=C$_7$H$_{15}$]

(a) n-heptyl L-2-[3-(5-benzyloxycarbonyloxy 3-indolyl)2-benzyloxycarbonylamino propionyloxy]acetate For 20 hours at ordinary temperature there was stirred:
50 g (0.1 mole) of L-3-(5-benzyloxycarbonyloxy 3-indolyl)2-benzyloxycarbonylamino propionic acid prepared according to Example 5-a,
20 ml of dicyclohexylamine (0.1 mole),
1 g of sodium iodide,
19.5 g (0.1 mole of n-heptyl chloracetate,
300 ml of dimethylformamide,
and it was then treated according to Example 1-b. After purification by chromatography on silica with a benzene ether mixture, 71% of crude oil was obtained having a single spot of Rf=0.55 in the usual solvent system and $[\alpha]_D^{22}$=−13°(absolute Ethanol 1%)

(b) n-heptyl L-2-[3-(5-hydroxy 3-indolyl)2-amino propionyloxy]acetate 32 g (0.05 mole) of the previously obtained product was hydrogenated in 400 ml of isopropanol in the presence of 2.5 g of 5% palladium on charcoal. When the theoretical amount of hydrogen had been fixed, the catalyst was filtered off, the solvent was evaporated, it was taken up again with ethyl acetate which was washed with water. After evaporation of this solvent the crude residue was recrystallized in benzene. 10 g of white crystals melting at 99° C. and $[\alpha]_D^{22} = -50.7°$-(acetone 1%), were obtained.

EXAMPLE 12 n-octyl L-2-[3-(5-hydroxy 3-indolyl)2-amino propionyloxy]acetate [(I), R=C$_8$H$_{17}$]

(a) n-octyl L-2-[3-(5-benzyloxycarbonyloxy 3-indolyl)2-benzyloxycarbonylamino propionyloxy]acetate The following mixture was stirred for 20 hours:
50 g (0.1 mole) (L) 3-(5-benzyloxycarbonyloxy 3-indolyl)2-benzyloxycarbonylamino propionic acid obtained as in paragraph 5-a,
300 ml of dimethylformamide,
20 ml of dicyclohexylamine
1 g of sodium iodide,
20.5 g (0.1 mole) of n-octyl chloracetate,
was treated according to Example 1-b.
51 g (77%) of crude oil was obtained having a single spot of Rf=0.6 in TLC on silica gel in the usual solvent system $[\alpha]_D^{25} = -13.9°(1\%$ Ethanol).

(b) n-octyl L-2-[3-(5-hydroxy 3-indolyl)2-amino propionyloxy]acetate 30 g (0.045 mole) of the product obtained in the preceding paragraph was hydrogenated in 400 ml of isopropyl alcohol in the presence of 2.5 g of 5% Palladium on charcoal. When the theoretical amount of hydrogen had been absorbed, the catalyst was filtered off, was evaporated to dryness, taken up with ether acetate and washed with water. After evaporation of the solvent, the crude residue was recrystallized in benzene. 10.9 g of white crystals were obtained (yield 48%) melting at 105° C. $[\alpha]_D = +0.71°$(absolute EtOH 1%), -52.0°(absolute acetone 1%).

EXAMPLE 13 n-dodecyl L-2-[3-(5-hydroxy 3-indolyl)2-amino propionyloxy]acetate [(I), R=C$_{12}$H$_{25}$]

(a) n-dodecyl L-2-[3-(5-hydroxy 3-indolyl)2-amino propionyloxy]acetate

The following mixture was stirred for 20 hours:
50 g (0.1 mole) of L-3-(5-benzyloxycarbonyloxy 3-indolyl)2-benzyloxycarbonylamino propionic acid prepared according to Example 5-a,
20 ml of dicyclohexylamine,
1 g of sodium iodide,
26.4 g of n-dodecyl chloracetate,
300 ml of dimethylformamide,
and it was then treated according to Example 1-b. The crude product was purified by chromatography on silica. The pure fraction only showed a single spot in TLC in the usual solvent system (yield 80%).

(b) n-dodecyl L-2-[3-(5-hydroxy 3-indolyl)2-amino propionyloxy]acetate

Under atmospheric pressure 77.4 g of the preceding product was hydrogenated in solution with 1.5 liter of isopropanol in the presence of 7 g of 5% palladium on charcoal. When the theoretical amount of hydrogen had been fixed, the catalyst was filtered off, it was evaporated to dryness, taken up again with ethyl acetate and washed with water. After evaporation of the solvent, the crude residue was crystallized twice in benzene. 60% of pure product of mp 107.5° C. $[\alpha]_D^{25} = +0.17°(1\%$ Ethanol) $[\alpha]_D^{25} = -42.2°(1\%$ acetone), was obtained.

EXAMPLE 14

(3,3-dimethyl)2-butyl L-2-[3-(5-hydroxy 3-indolyl)2-amino propionyloxy]acetate

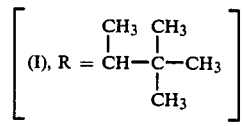

$$(I), R = CH-\underset{\underset{CH_3}{|}}{\overset{\overset{CH_3}{|}}{C}}-CH_3$$

(a) (3,3-dimethyl)2-butyl chloracetate 47.5 g (0.42 mole) of chloracetyl chloride was slowly added to a mixture of 40.9 g (0.4 mole) of 3,3-dimethyl 2-butanol and 58 ml (0.42 mole) of triethylamine. The reaction mixture kept at 10° C. during the running in of the acid chloride, was brought to ordinary temperature and stirred for about 4 hours. After filtration and washing with ether of triethylamine hydrochloride, the solution was washed with water then dried over sodium sulfate. After evaporation of the solvent and distillation of the vacuum, 64 g namely 89% was obtained of a pure liquid of b.p.$^t$=79°/81° C. under 20 mm Hg.

(b) (3,3-dimethyl)2-butyl L-2-[3-(5-benzyloxycarbonyloxy 3-indolyl)2-benzyloxycarbonylamino propionyloxy]acetate The following mixture was stirred for 20 hours at ordinary temperature:
50 g (0.1 mole) of L-3-(5-benzyloxycarbonyloxy 3-indolyl)2-benzyloxycarbonylamino propionic acid,
20 ml (0.1 mole) of dicyclohexylamine,
1 g of sodium iodide,
17.75 g (0.1 mole of (3,3-dimethyl)2-butyl chloracetate
300 ml of dimethylformamide,
and then treated according to Example 1-b. The crude product was purified by chromatography on silica with a mixture of toluene 9 p., ether 1, as eluant. 76% of a pure oil was obtained having a single spot in TLC on Kieselgel in the various systems, among others the mixture: chloroform 70, Ethanol 30, formic acid 2 (Rf=0.6) and $[\alpha]_D^{25} = -7.28°$(Ethanol 1%).

(c) (3.3-dimethyl)2-butyl L-2-[3-(5-hydroxy 3-indolyl)2-amino propionyloxy]acetate Under atmospheric pressure 48 g of the preceding product was hydrogenated in solution in one liter of isopropanol in the presence of 2.5 g of 5% palladium on charcoal. When the theoretical amount of hydrogen had been fixed, the catalyst was filtered off, it was evaporated to dryness and taken up with ethyl acetate which was washed with water. After evaporation of the solvent, it was re-crystallized in benzene and there were obtained 14.5 g (53%) of white crystals of mp 106°/7° C. $[\alpha]_D^{25} = +7°.48(1\%$ acetone).

EXAMPLE 15

1-adamantyl methyl 2-[3-(5-hydroxy 3-indolyl)2-amino propionyloxy]acetate

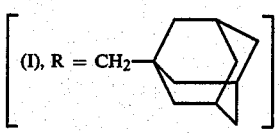

(a) 1-adamantyl methyl L-2[3-(5-benzyloxycarbonyloxy 3-indolyl)2-benzyloxycarbonylamino propionyloxy]acetate For 20 hours at ordinary temperature the following mixture was stirred:
50 g (0.1 mole) L-3(5-benzyloxycarbonyloxy 3-indolyl)2-benzyloxycarbonylamino propionic acid,
20 ml dicyclohexylamine (0.1 mole)
24.3 g chloracetate 1-adamantyl methyl
1 g sodium iodide
500 ml of dimethylformamide,
then treated according to example 1-b. The residual crude oil was purified by chromatography on silica by eluting with a toluene/ether mixture. 77% of pure product was obtained having a single spot by TLC of silica gel in the usual system $[\alpha]_D^{25} = -8°$(Ethanol 1%).

(b) 1-adamantyl methyl L-2-[3-(5-hydroxy 3-indolyl)2-amino propionyloxy]acetate

Under atmospheric pressure 36 g of the preceding product was hydrogenated in solution in 600 ml of isopropyl alcohol in the presence of 2.5 g of 5% palladium on charcoal. When the theoretical amount of hydrogen had been fixed, the catalsyt was filtered off, the solvent was evaporated off and it was taken up in ethyl acetate. After washing with water and treated in the dark, it was evaporated to dryness. It was re-crystallized in benzene and 68% of product melting at 134° C. was obtained and of $[\alpha]_D^{25} = -0.7°$(Ethanol 1%) and $[\alpha]_D^{25} = -26.1°$-(Acetone 1%).

EXAMPLE 16

1-adamantyl L-2[3-(5-hydroxy 3-indolyl)2-amino propionyloxy]acetate

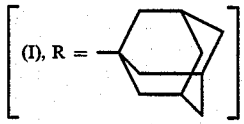

(a) 1adamantyl chloracetate

There was added slowly at 10° C. and under nitrogen 24 ml of chloracetyl chloride to 30.5 g (0.2 mole) of 1-adamantanol and 12 g of magnesia in suspension in 400 ml of chloroform; it was then brought under reflux for some hours. It was cooled, the inorganic material was filtered off and the solvent evaporated. The crude product was crystallized in hexane. 90% of the product melting 79° C. (capillary) was obtained.

(b) 1-adamantyl L-2[3-(5-benzyloxycarbonyloxy 3-indolyl)2-benzyloxycarbonylamino propionyloxy]acetate For 20 hours at ordinary temperature the following mixture was stirred:
41.6 g (0.085 mole)L-3(5-benzyloxycarbonyloxy 3-indolyl)2-benzyloxycarbonylamino propionic acid,
20 ml dicyclohexylamine (0.1 mole),
19.5 g 1-adamantyl chloracetate
1 g sodium iodide
500 ml of dimethylformamide,
then it was processed according to example 1-b. The residual oil was purified by chromatography on silica by eluting with a toluene/ether mixture. 62% of pure product having a single spot of RF 0.6 in the usual system was obtained and $[\alpha]_D^{22} = -15°85$ (ethanol 1%).

cl (c) 1-adamantyl L-2[3-(5-hydroxy 3-indolyl)2-amino propionyloxy]acetate

Under atmospheric pressure 35.5 g (0.052 mole) of the product obtained from paragraph 16-b was hydrogenated in solution in 600 ml of isopropanol and in the presence of 4 g of 5% palladium on charcoal. When the theoretical amount of hydrogen had been fixed, the catalyst was filtered off, the solvent was evaporated and it was taken up again in ethyl acetate. After washing in water. It was evaporated to dryness then re-crystallized in a benzene hexane mixture. 57% of crystallized product was obtained melting at 90° C. (dec.) $_D = 9.7°$(0.5 acetone).

EXAMPLE 17

L-2[3-(5-hydroxy 3-indolyl)2-amino propionyloxy]acetic acid [(I); R=H]

(a) L-2[3-(5-benzyloxycarbonyloxy 3-indolyl)2-benzyloxycarbonylamino propionyloxy]benzyl acetate For 20 hours at ordinary temperature there was stirred:
50 g (0.1 mole) L-3(5-benzyloxycarbonyloxy 3-indolyl)2-benzyloxycarbonylamino propionic acid,
20 ml dicyclohexylamine,
18.45 g (0.1 mole) benzyl chloracetate,
1 g sodium iodide,
300 ml dimethylformamide,
was then treated according to example 1-b. The crude oil was purified by chromatography on silica with a benzene ether mixture as eluant. 66% of a product was obtained showing a single spot of Rf=0.54 in TLC on silica gel in the usual solvent system $[\alpha]_D^{25} = -14.73°$(1% ethanol).

(b) L-2[3-(5-hydroxy 3-indolyl)2-amino propionyloxy]acetic acid

Under atmospheric pressure 36 g (0.056 mole) of the preceding product was hydrogenated in solution in 700 ml of isopropanol and 150 ml of chloroform in the presence of 4 g of 5% palladium on charcoal. When the hydrogen absorption was finished, the solvents were evaporated off, it was taken up again in water brought to pH 7.0 with dilute ammonia and then extracted with ethyl acetate.

After evaporation of the solvent, the product was purified by washing with water and with acetone. 33% of pure product was obtained melting at 204°/205° C. $[\alpha]_D^{22} = +29.6°$[1%, NH$_4$OH,N/10].

The compounds according to the invention show remarkable pharmacological activities, in particular on the central nervous system. Table 1 below summarises the biochemical assay of endogenous serotonin in the brain of rats. These assays were carried out after administration orally of a single dose at 10 mg/kg in Wistar male adult rats.

TABLE 1

| Compounds of the examples | 6b | 8b | 12b | 13b | 15b | 14c | (L)5 HTP control |
|---|---|---|---|---|---|---|---|
| % increase of brain serotonin | 22 | 20 | 15 | 26 | 17 | 32 | 10 |

It is undeniable that the activity of the compounds according to the invention is distinctly higher than that of 5 HTP.

TOXICITY

The acute toxicities of the derivatives according to the invention in the mouse are very much less than those of L 5-HTP. Thus the $LD_{50}$'s of all of the compounds according to the invention are higher than 1250 mg/kg, whereas the $LD_{50}$ (orally) of L 5-HTP is equal to 700 mg/kg.

It results from the foregoing description that whatever the methods of application or administration, the derivatives of 2-[3-(3-indolyl)2-amino propionyloxy]acetic acid have, with respect to the previously known 5-HTP, numerous advantages and particularly that of higher activity, due principally to their resistance to peripheral decarboxylase.

We claim:

1. A process for the preparation of a compound of the formula I:

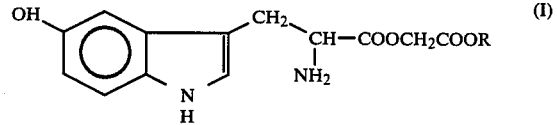

wherein R is
a hydrogen atom,
a linear or branched alkyl radical having 1 to 12 atoms,
a member of the group consisting of a mono-alicyclic radical having 5-16 carbon atoms, an adamantyl radical or an adamantyl radical linked by a methylene radical or a pharmaceutically acceptable addition salt thereof,
from 5-hydroxytrytophane, said process comprising:
blocking both the 5-hydroxy and the alpha amino function or only the alpha-amino function of 5-hydroxytryptophane by reacting said 5-hydroxytryptophane with a compound of the formula $R_2O$-COX where $R_2$ represents a benzyl radical, which acts to block the 5-hydroxy and alpha-amino or only the alpha-amino function, and X represents a halogen atom, at a pH of about 9.5;
esterifying the acid function of the thus blocked 5-hydroxytryptophane by reacting said blocked 5-hydroxytryptophane with a compound corresponding to the formula:

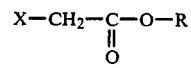

in which:
R and X have the same meaning as defined above, in an aprotic solvent containing an equimolar amount of dicyclohexylamine and;
then unblocking the 5-hydroxy or alpha-amino function by catalytic hydrogenation of said esterified and blocked 5-hydroxytryptophane to replace any $R_2OCO$— radical with a hydrogen atom;
isolating said compound of formula (I).

2. Process according to claim 1, wherein the amine or phenol functions are blocked by means of reagents taken from the group which comprises

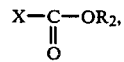

$R_2$ and X having the same meaning as previously.

3. Process according to claim 1, wherein the condensation of the 3-(5-hydroxy 3-indolyl) acid derivatives is affected with the blocking agent

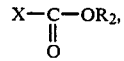

in the presence of a base which is an acceptor for a hydrohalic acid and in an aprotic solvent.

4. Process according to claim 1, where in the unblocking of the $NH_2$ or OH functions is carried out by catalytic hydrogenation.

5. Process for preparing a compound according to claim 1, wherein X is a chlorine atom.

6. Process according to claim 5, wherein the amino or 5-hydroxy functions are blocked by means of reagents taken from the group which comrpises

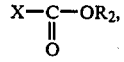

$R_2$ and X having the same meaning as previously.

7. Process according to claim 5, wherein the condensation of 3-(5-hydroxy 3indolyl) acid derivatives is effected with the blocking agent

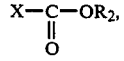

in the presence of a base which is an acceptor for a hydrohalic acid and in an aprotic solvent.

* * * * *